(12) United States Patent
Bates

(10) Patent No.: US 8,936,542 B1
(45) Date of Patent: Jan. 20, 2015

(54) CYCLOMAGNETIC THERAPY

(75) Inventor: Kerry M. Bates, Newcastle, OK (US)

(73) Assignee: Cyclomagnetics LLC, Newcastle, OK (US)

( * ) Notice: Subject to any disclaimer, the term of this patent is extended or adjusted under 35 U.S.C. 154(b) by 268 days.

(21) Appl. No.: 13/406,940

(22) Filed: Feb. 28, 2012

Related U.S. Application Data

(60) Provisional application No. 61/448,704, filed on Mar. 3, 2011.

(51) Int. Cl.
A61N 2/06 (2006.01)
A61H 23/02 (2006.01)
A61N 2/00 (2006.01)

(52) U.S. Cl.
CPC ..................... *A61N 2/002* (2013.01)
USPC .......................................... 600/9

(58) Field of Classification Search
CPC ............. A61N 2/00; A61N 2/02; A61N 2/06; A61N 2/12; A61N 2/002; A61N 2/004; A61N 2/006; A61N 2/008
USPC ............... 600/9–15; 601/15, 40, 72
See application file for complete search history.

(56) References Cited

U.S. PATENT DOCUMENTS

| | | | | |
|---|---|---|---|---|
| 3,626,223 | A * | 12/1971 | Maier | 310/153 |
| 5,341,057 | A * | 8/1994 | Yamaguchi et al. | 310/81 |
| 5,562,706 | A * | 10/1996 | Lauterbach et al. | 607/3 |
| 5,871,438 | A | 2/1999 | Ardizzone | |
| 6,001,055 | A | 12/1999 | Souder | |
| 6,065,210 | A | 5/2000 | Bove | |
| 6,102,875 | A | 8/2000 | Jones | |
| 6,320,488 | B1 | 11/2001 | Leupold | |
| 6,436,029 | B1 * | 8/2002 | Benderev | 600/30 |
| 6,461,377 | B1 | 10/2002 | An | |
| 6,537,196 | B1 | 3/2003 | Creighton, IV et al. | |
| 6,663,557 | B2 | 12/2003 | Werny | |
| 6,679,825 | B2 * | 1/2004 | Alicea | 600/9 |
| 6,796,937 | B1 | 9/2004 | Bates | |
| 7,507,198 | B2 | 3/2009 | Ardizzone et al. | |
| 7,648,454 | B2 * | 1/2010 | Sotiriou | 600/15 |
| 2006/0028077 | A1 * | 2/2006 | Yamaguchi et al. | 310/81 |
| 2007/0261216 | A1 * | 11/2007 | Pauli | 24/530 |
| 2011/0230802 | A1 * | 9/2011 | Nan | 601/46 |

OTHER PUBLICATIONS

"glue". The American Heritage Dictionary of the English Language Fourth Edition. 2003. Houghton Mifflin Company, Jan. 10, 2014. http://www.thefreedictionary.com/glue.*

* cited by examiner

*Primary Examiner* — Christine H Matthews
*Assistant Examiner* — Joshua D Lannu
(74) *Attorney, Agent, or Firm* — Molly D. McKay

(57) ABSTRACT

A cyclomagnetic device for use in cyclomagnetic therapy. The device has a head and tail connected by a handgrip and is housed in housing in the shape of a showerhead. Inside the head end, a variable speed DC motor turns a rotor to which magnets are attached in a unipolar and unbalanced arrangement so that the rotor vibrates when the rotor turns. Inside the tail end is a pressure/trigger point massage tool. A battery pack that provides power to the motor is located in the handgrip. A dual switch attached to an electronic card connects the batteries to the motor that operates the device. To provide comfort when the device is used on the body, a soft rubber cushioned band is provided around the edge of the head and a soft rubber boot covers the tail of the device.

5 Claims, 3 Drawing Sheets

CYCLOMAGNETIC THERAPY

CROSS-REFERENCE TO RELATED APPLICATIONS

The present application claims priority to Provisional Patent Application Ser. No. 61/448,704 for Cyclomagnetic Therapy filed on Mar. 3, 2011.

BACKGROUND OF THE INVENTION

1. Field of the Invention

The present invention relates to a cyclomagnetic therapeutic device. More specifically, the present invention employs out of balance rotating magnets to produce a vibrating magnetic field that can be used for magnetic therapy.

2. Description of the Related Art

Magnetic therapy involves use of magnetic fields on the body for therapeutic purposes. There are several theories on how magnetic therapy affects the body.

One theory suggests that the iron in the red blood cells of the blood is drawn to the magnetic field, thereby supplying more oxygen and nutrients to the treated area of the body. Another theory suggests that magnets somehow stimulate the brain and affects the pineal gland.

Still another theory focuses on the fact that our bodies are electrical systems, and each of the cells of the body depends on electrical currents to function effectively. Death occurs when the body ceases to have any electrical activity. The theory is that certain magnetic fields can induce or amplify the beneficial electrical currents that help the body's systems, organs, and cells function properly.

A further theory relates to the use of magnetic therapy for thousands of years in Chinese medicine. It is theorized that magnets are able to break up stagnation by rearranging energy (Qi) into an organized manner so that it can flow freely. This is similar to the way shards of steel are organized and all face one direction after a magnet is passed over them.

Still a further theory is that magnetic therapy causes the blood to agitate, causing heat to be generated that allows the blood to flow better. This is an effect similar to the use of a heating pad on the body for therapy.

There are many applications claimed for magnetic therapy from the reduction of scar tissue to the treatment of internal organs. However, the predominant use of magnetic devices is in the treatment of musculoskeletal pain and myofacial pain. While the mechanism by which magnetic therapy produces pain relief is subject to much conjecture, there is a consensus that heightened blood flow to the area under the footprint of the magnet is one of the primary results of magnetic treatment. These results have been demonstrated by both thermographic and nuclear medicine studies.

There has also been evidence of pain blocking phenomena in certain nerve fibers related to the application of magnetic fields. Researchers have been able to demonstrate changes in the electrical potential of nerve cells which raise the threshold for transmitting pain impulses as a result of magnetic fields. Some scientists subscribe to the Hall Effect which promotes the idea that ions in the blood are manipulated by magnetic fields, thus producing a heating effect in the magnetized area and increasing blood circulation. The Hall Effect is the theoretical basis for the present invention. Simply stated, the Hall Effect subscribes to the idea that when therapeutic magnets are used correctly, an ionic charge is established in the blood, blood cells, blood particles, and tissue mass. The rotating magnets of the present invention are placed so that the positive field of the device is facing the body, thereby causing the blood, flesh, muscles and other body tissue to take on an opposite negative ionic charge. Because the present invention uses only a positive magnetic field, it is considered to be a unipolar device.

Other scientists disagree and insist that, from a biological perspective; magnets activate or turn on capillaries creating extra blood supply at the cellular level as opposed to the older notion that magnets produce a local heating effect to stimulate blood supply which is essentially what the Hall Effect is about.

Regardless of the exact mechanism by which magnetic therapy works, it is generally accepted that it does work.

The present invention uses unbalanced rotating magnets that create a strong vibration along with a rotating unipolar magnetic field. This strong vibration penetrates deep into muscle tissue, causing the unit to feel like a much larger and heavier vibrating unit. This unipolar magnetic therapy massaging device can be used for magnetic therapy in the treatment of pain. More specifically, the device can be used for muscle therapy, circulation therapy and massage therapy.

SUMMARY OF THE INVENTION

The present invention is a cyclomagnetic device for use in cyclomagnetic therapy. The device has one DC electric motor, a set of rechargeable batteries, a variable speed control switch controlled by an electronic control card, a multi-finger rotor with attached magnets which rotates at different speeds located on a head end of the device, and a magnetic pressure/trigger point massage tool located on a tail end of the device.

Each of the fingers on the rotor has one bar or disc magnet attached to it using a combined positive rotating unipolar magnetic field facing toward the front face of the device. The rotor has two plates made of ferrous material (iron steel) used to hold and disperse the magnetic field (diffused unipolar magnetic field). The spherical magnetic pressure/trigger point massaging device has one large neodymium magnet located inside it with the positive field facing out toward the tail of the device.

In the preferred embodiment of the device, the magnets are attached to a three finger rotor. The device is enclosed in a molded ABS plastic housing with the battery pack located in the handgrip. The motor and rotor are located inside the housing at the head of the device. The pressure tool is located at the tail of the device. The housing is shaped like a showerhead and has a variable speed control switch located in it which connects the batteries to the internal DC motor via an electronic control card. An LED light at the variable speed control switch indicates that the unit is turned on. A motor plate holds the motor to the housing for security.

The rotor and magnets attach to a shaft of the motor in the center of the rotor. A rounded cover or domed cap, also constructed of ABS plastic with a rubber cushion band around the edge, extends over the head of the device and over the magnetic rotor to provide comfort when used on curved areas of the body. The domed cap is glued to the housing instead of using metallic screws which could interfere with the strong magnetic field being generated. The magnetic pressure/trigger point massaging end is also covered with a rubber boot for comfort.

By displacing one magnet off-center on the rotor, the rotor is thrown off-balance creating a vibrating effect and allowing the device to also become a physical vibrating device used for deep muscle massaging therapy. With each revolution of the magnet rotor, the body tissue and cells are also magnetically vibrated.

DETAILED DESCRIPTION OF THE PREFERRED EMBODIMENT

Figure 1:
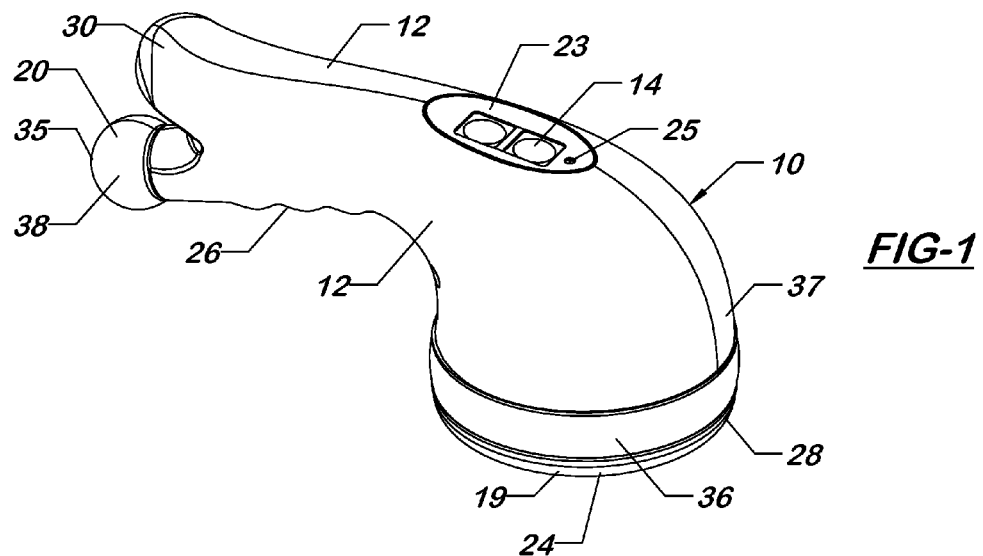
FIG. 1 is a perspective view of a cyclomagnetic therapeutic device constructed in accordance with a preferred embodiment of the present invention.
Figure 2:
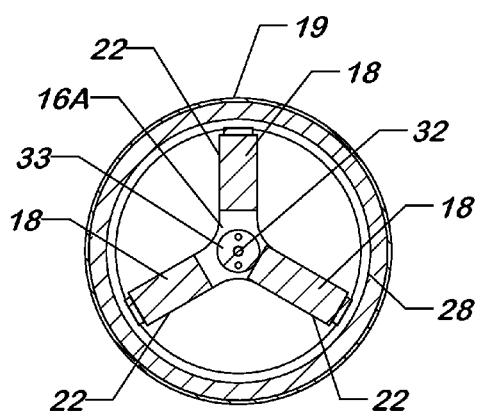
FIG. 2 is a partially cut away view of the head of the device of FIG. 1 showing a three finger rotor.

Referring now to the drawings and initially to FIGS. 1, 3 and 5-9, there is illustrated a cyclomagnetic device 10 for use in cyclomagnetic therapy that is constructed in accordance with a preferred embodiment of the present invention. FIGS. 2 and 4 illustrate an alternate embodiment of the invention. The preferred embodiment and the alternate embodiment differ only in that a three arm rotor 16A is employed with the preferred embodiment, whereas a four arm rotor 16B is employed with the alternate embodiment. Both embodiments will be hereafter referred to as the device 10.

The device 10 has one DC electric motor 11 located within a housing 12 for the device 10, a set of rechargeable batteries 13 also located within the housing 12, a variable speed control switch 14, a multi-finger rotor 16A or 16B with attached magnets 18 which rotates at different speeds, and a magnetic pressure/trigger point massage tool 20. The rotor 16A or 16B is comprised of an upper plate 31A and a lower plate 31B between which are sandwiched magnets 18 and a central hub 33. The central hub 33 is attached to a shaft 32 of the motor 11 as a means of turning the rotor 16A and 16B.

Each of the fingers 22 on the rotor 16A or 16B has one or more preferably neodymium bar or disc magnets 18 attached to it using a combined positive rotating unipolar magnetic field facing toward the front face 24 of the device 10 and toward the person being treated. The spherical magnetic pressure/trigger point massaging tool 20 has one large preferably neodymium magnet 34 located inside it with the positive field facing out toward the rear end 35 of the device 10 and toward the person being treated. The dual-purpose magnetic pressure/trigger point massaging tool 20 is used to apply pressure to specific points on the body and as a counterbalance weight to make the device 10 more comfortable to operate. The device's dual functioning approach is used to increase blood circulation, relax muscles, reduce stress, reduce inflammation and reduce pain.

As illustrated in FIG. 2, in the preferred embodiment of the device 10, the magnets 18 are attached to a three finger rotor 16A. The rotating rotor 16A creates a defused unified magnetic field for treatment. The device 10 is enclosed in a molded ABS plastic housing 12 with the battery pack 13 located within the handgrip portion 26 of the housing 12. The motor 11 and rotor 16A or 16B are located inside the housing 12 at the head 28 of the device 10. The pressure tool 20 is located at the tail 30 of the device 10. The housing 12 is preferably shaped like a showerhead and has the variable speed dome or button control switch 14 located in it.

Referring now to FIG. 4, the variable speed control switch 14 electrically connects to an electronic control card 21 via electrical connection 15A. A switch cover 23 having a pair of openings therein that allow access to the switch 14 is provided on the housing 12 over the switch 14. The electronic control card 21, in turn, connects to the batteries 13 via electrical connection 15B and to the internal DC motor 11 via electrical connection 15C as a means of controlling the function of the motor 11. An LED light 25 located in association with the variable speed control switch 14 indicates the device 10 is turned on. A motor mounting plate 17 attaches the motor 11 to the inside of the housing 12 for security.

A rounded cover or domed cap 19 is located over the rotor 16A or 16B forming the head 28 of the device 10. The domed cap 19 is made of ABS plastic and has a rubber cushion band 36 around the edge to provide comfort when used on curved areas of the body, such as the neck area.

Figure 3:
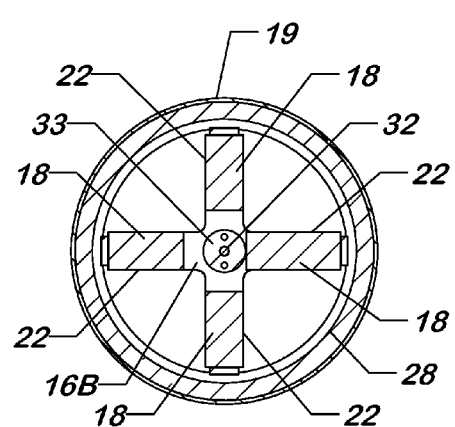
FIG. 3 is a partially cut away view of an alternate head of the device of FIG. 1 showing a four finger rotor.
Figure 4:
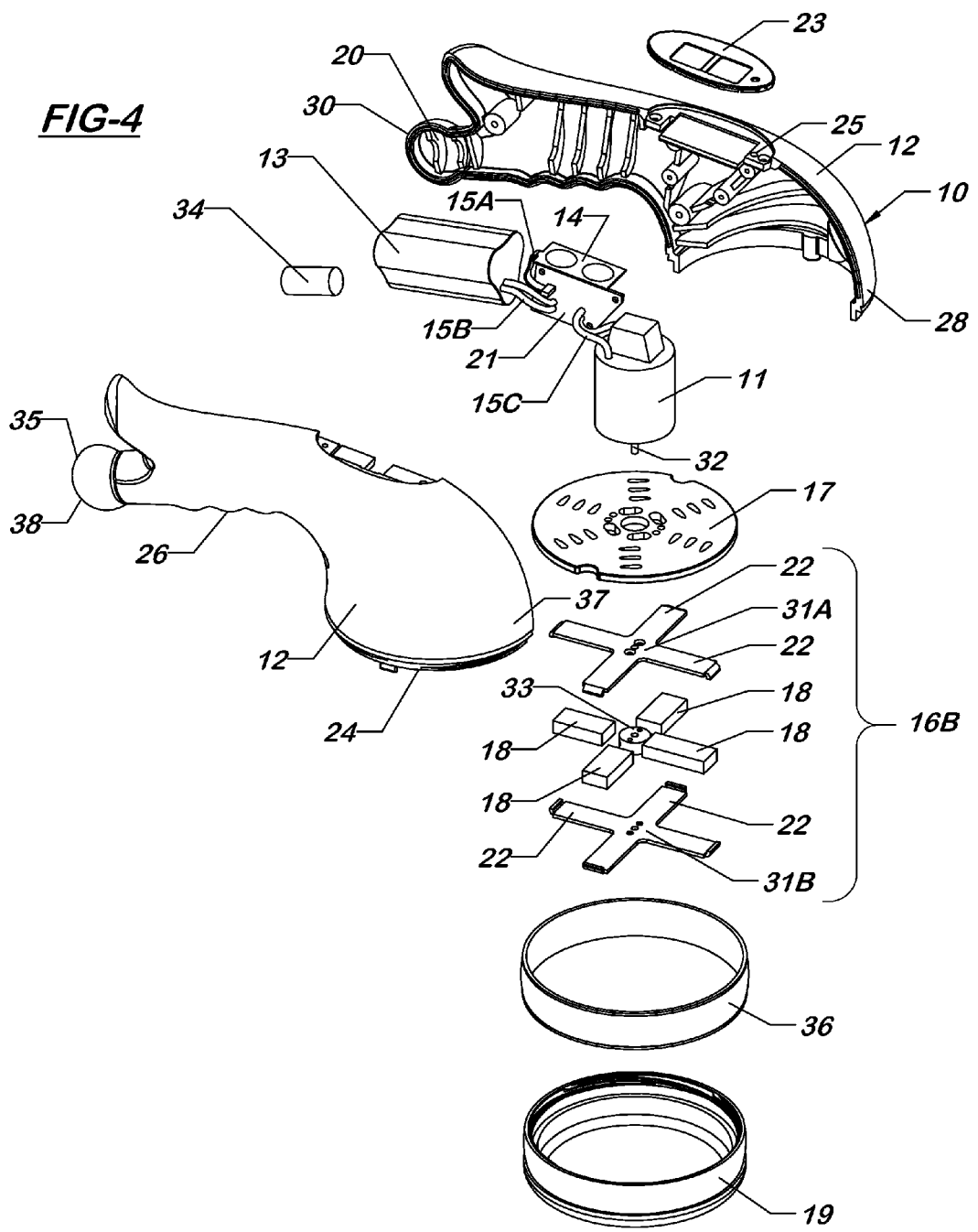
FIG. 4 is an exploded view of the cyclomagnetic therapeutic device of FIG. 1 showing use of a four finger rotor.
Figure 5:
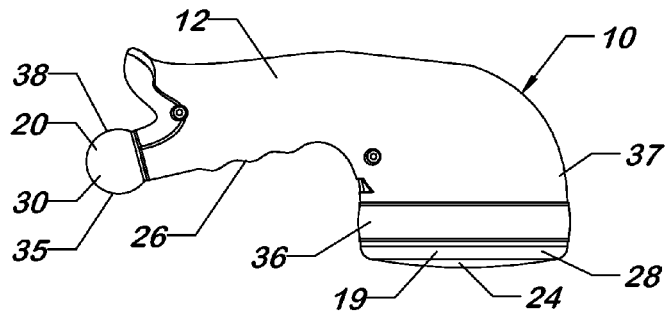
FIG. 5 is a right side view of the device of FIG. 1.
Figure 6:
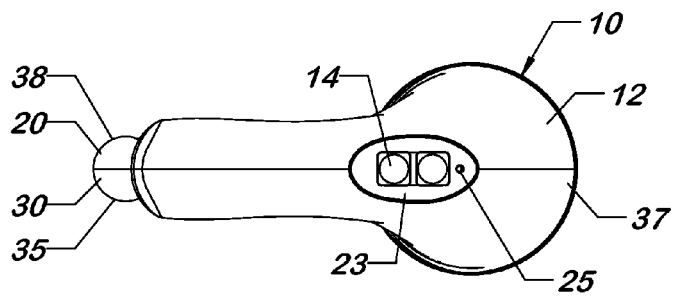
FIG. 6 is a top plan view of the device of FIG. 5.
Figure 7:
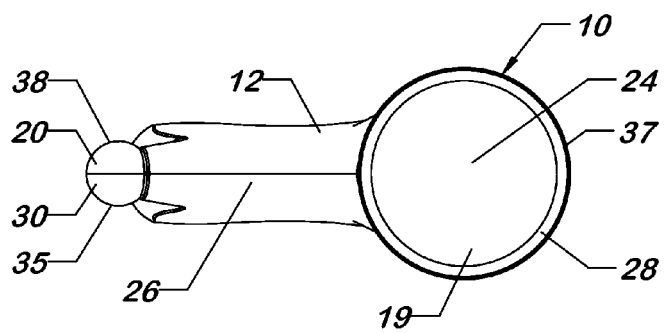
FIG. 7 is a bottom plan view of the device of FIG. 5.
Figure 8:
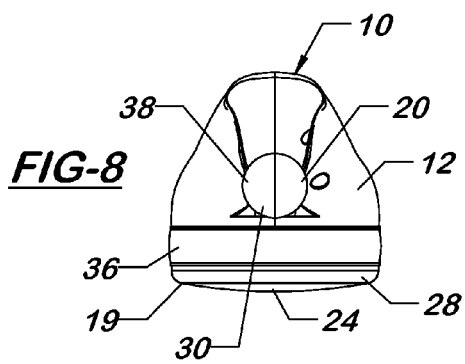
FIG. 8 is a rear end view of the device of FIG. 5.
Figure 9:
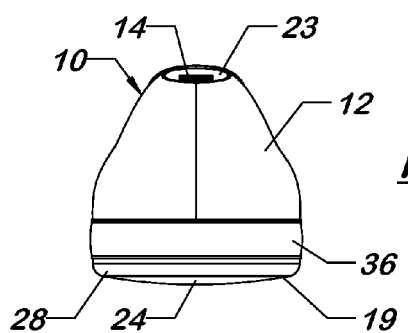
FIG. 9 is a front end view of the device of FIG. 5.

Referring to FIGS. 2 and 3, there are shown, respectively, a three finger rotor 16A and an alternate four finger rotor 16B with the domed cap 19 removed on each. A hub 33 provided at the center of the magnets 18 in the rotor 16A or 16B attaches to a shaft 32 of the motor 11 as a means of rotating the rotor 16A or 16B. The domed cap 19 is glued to the housing 12 instead of using metallic screws that could interfere with the strong magnetic field being generated. The magnetic pressure/trigger point massaging tool 20 is also provided with a ball or cover 38 of rubber or similar material forming a boot for comfort on the tool 20.

By displacing one of the magnets 18 off-center on the rotor 16A or 16B, the rotor 16A or 16B is thrown off-balance creating a vibrating effect. The device 10 now also becomes a physical vibrating instrument used for deep muscle massaging therapy. With each revolution of the magnet rotor 16A or 16B, the body tissue and cells are also magnetically vibrated.

Although the invention has been described for use on humans, it is not so limited, and the invention can be scalable to be used on animals, both large and small, for the same results as in humans.

While the invention has been described with a certain degree of particularity, it is manifest that many changes may be made in the details of construction, operation, and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A cyclomagnetic therapeutic device comprising:
    a housing containing a multi-finger rotor with several attached magnets, the rotor is operatively attached to a DC electric motor, wherein the rotor is configured to be thrown off-balance and to create a vibrating effect as it rotates by having at least one of the magnets being displaced off-center on the rotor,
    a power source configured to supply power to the DC electric motor to turn the rotor,
    a switch configured to control operation of the DC electric motor,
    an electronic control card, wherein said electronic control card electrically connects the switch, the DC electric motor, and the power source,
    a domed cap located over the rotor, the domed cap and rotor forming a head massage element which is designed for contact with an area of a body,
    a magnetic pressure/trigger point massage tool provided on a tail of the housing forming a tail massage element, wherein a magnet is provided within said tail massage element, said tail massage element of the housing being located on an opposite end of the housing from the head massage element, said magnetic pressure/trigger point massage tool being configured to apply pressure to specific points on the body, a cushion cover forming a boot for comfort on the tool, a hand grip portion of the housing for holding the housing, said hand grip portion being located centrally between a head of the housing and the tail of the housing, and an enlarged area of the housing provided adjacent to the tail massage element wherein said enlarged area is configured to prevent a user's hand from slipping off of the hand grip, wherein said enlarged area is a surface against which the user's hand can press to apply pressure with the tail massage element.

2. A cyclomagnetic therapeutic device according to claim 1 further comprising:

the magnetic pressure/trigger point massage tool being spherical, said magnet located inside the tail is in association with the pressure/trigger point massaging tool, said magnet producing a positive magnetic field facing out toward a rear end of the device.

3. A cyclomagnetic therapeutic device according to claim 1 further comprising:

a central handgrip portion provided on the housing midway between the head and tail, and said magnetic pressure/trigger point massage tool serving as a counterbalance weight to the rotor located in the head of the housing to make the device more comfortable to operate.

4. A cyclomagnetic therapeutic device according to claim 3 wherein the housing is shaped like a hand held showerhead.

5. A cyclomagnetic therapeutic device according to claim 1 further comprising:

said multi-finger rotor provided with an upper plate and a lower plate between which are sandwiched the magnets and a central hub.

\* \* \* \* \*